United States Patent [19]

Baldwin

[11] 4,281,005
[45] Jul. 28, 1981

[54] NOVEL 2-PYRIDYLIMIDAZOLE COMPOUNDS

[75] Inventor: John J. Baldwin, Lansdale, Pa.

[73] Assignee: Merck & Co., Inc., Rahway, N.J.

[21] Appl. No.: 157,927

[22] Filed: Jun. 6, 1980

Related U.S. Application Data

[63] Continuation of Ser. No. 17,877, Mar. 5, 1979, abandoned, which is a continuation-in-part of Ser. No. 891,662, Mar. 30, 1978, abandoned, which is a continuation-in-part of Ser. No. 755,777, Dec. 30, 1976, abandoned.

[51] Int. Cl.³ .................. A61K 31/415; C07D 401/02
[52] U.S. Cl. .................................. 424/263; 546/113; 546/278
[58] Field of Search ...................... 546/278; 424/263

[56] References Cited

U.S. PATENT DOCUMENTS

| | | | |
|---|---|---|---|
| 2,505,247 | 4/1950 | Isler | 260/309.6 |
| 2,847,417 | 8/1958 | Erner | 260/309 |
| 3,691,178 | 9/1972 | Baldwin | 546/278 OR |
| 3,786,061 | 1/1974 | Novello et al. | 546/278 OR |
| 4,058,614 | 11/1977 | Baldwin | 546/278 X |

FOREIGN PATENT DOCUMENTS

| | | |
|---|---|---|
| 42-1546 | 1/1967 | Japan . |
| 1465946 | 3/1977 | United Kingdom . |

OTHER PUBLICATIONS

Fromherz et al., Chem. Abstracts, vol. 42, cols. 8956–8957 (1948).
Fromherz et al., Helv. Physiol. et Pharmacol. Acta, vol. 6, pp. 42–54 (1948).
Baldwin et al., III, J. Hed. Chem. 18, 895–900 (1975).
Ciba, C. A. 58 2455e (1963).
Case, J. Het. Chem. 4, 157–159 (1967).
Sawa (I), J. Chem. Soc. 66, 89791u (1967).
Baldwin IV–C. A. 83, 114406f (1975).
Sawa II–C. A. 20, 28867g (1969).
Sawa III–J. Chem. Soc. (JAP) 89, 868–872 (1968).
Oxley et al.–C. A. 41, 5466d (1947).
Ciba–C. A. 43, 5048–5049 (1949).
Castle, R–C. A. 52, 18393–18394 (1958).
Roberts, J. D.–Basic Principles of Org. Chem., W. A. Benjamin ing–N. Y.–Amst.–pp. 70–71 (1965).
Goodman; L. et al.–Pharm. Basis of Therapeutics MacMillan Co., 506–507 (1970).

*Primary Examiner*—John D. Randolph
*Attorney, Agent, or Firm*—Daniel T. Szura; Harry E. Westlake, Jr.

[57] ABSTRACT

Novel alkylsubstituted 2-pyridylimidazoles, halosubstituted-2-pyridylbenzimidazoles, and 2-pyridylimidazopyridines are disclosed. The compounds have pharmaceutical utility as xanthine oxidase inhibitors and/or as antihypertensive.

6 Claims, No Drawings

NOVEL 2-PYRIDYLIMIDAZOLE COMPOUNDS

CROSS REFERENCE TO RELATED APPLICATIONS

This is a continuation of application Ser. No. 017,877, now abandoned, filed Mar. 5, 1979, which in turn is a continuation-in-part of application Ser. No. 891,622, filed Mar. 30, 1978, now abandoned, which in turn is a continuation-in-part of application Ser. No. 755,777, filed Dec. 30, 1976, now abandoned.

BACKGROUND OF THE INVENTION

This invention is concerned with novel 4-alkyl-2-pyridylimidazoles, benzimidazoles and imidazopyridines having pharmaceutical activity.

2,4(or 5)-Disubstituted imidazoles, excluding 4-alkyl imidazoles, are disclosed in U.S. Pat. No. 3,691,178. These compounds are shown to have xanthine oxidase inhibiting activity, which indicates usefulness for treating gout or hyperuricemia. U.S. Pat. No. 3,786,061 and Journal of Medicinal Chemistry, 18, 895–900 (1975) dislcose 4(5)-trifluoromethyl-2-pyridiylimidazoles which are shown to have xanthine oxidase and/or antihypertensive activity. No 4-alkyl-2-substituted imidazoles are disclosed.

Certain 2-pyridylbenzimidazoles useful as light screening agents are disclosed in Chemical Abstracts, 58, 2455-e (1963).

2-(2-Pyridyl)-1H-imidazo[4,5-c]pyridines are disclosed in the Journal of Heterocyclic Chemistry, 4, 157–159 (1967). No utility is disclosed for these pyridines.

2-(3-Pyridyl)imidazole is disclosed by Fromherz et al in Helv. Physiol. Acta 6 42–54 (1948) and also Chemical Abstracts 42, 8956i (1948). No alkylimidazole derivatives are suggested.

Certain novel alkyl-2-pyridylimidazoles, halo-2-pyridylbenzimidazoles, and 2-pyridylimidazopyridines have been discovered which exhibit antihypertensive and/or xanthine oxidase inhibiting activity.

SUMMARY OF THE INVENTION

4-Alkyl-2-pyridylimidazoles, 2-pyridylbenzimidazoles, and 2-pyridylimidazopyridines and their use for treating hypertension and/or gout or hyperuricemia.

DESCRIPTION OF PREFERRED EMBODIMENT

An embodiment of this invention is compounds selected from the group consisting of:

(a) substituted imidazoles having the formula:

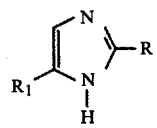

wherein R is 3-pyridyl or 4-pyridyl and $R_1$ is $C_1$-$C_5$ alkyl, branched and unbranched, e.g. t-butyl, n-pentyl, isopropyl, and pharmaceutically acceptable salts thereof;

(b) halobenzimidazoles having the formula:

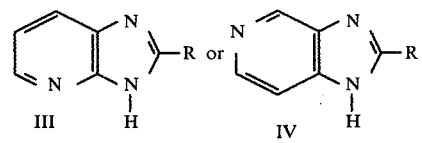

wherein R is 3-pyridyl or 4-pyridyl, $R_2$ is bromo or chloro, and $R_3$ is hydrogen, bromo or chloro, and pharmaceutically acceptable salts thereof; and (c) imidazopyridines having the formula:

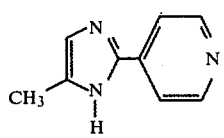

wherein R is 3-pyridyl or 4-pyridyl, and pharmaceutically acceptable salts thereof.

The pharmaceutically acceptable salts include metal salts, e.g. Na, K, the alkaline earth metals; quaternary salts and acid addition salts of the Formula I-IV compounds. The metal salts can be prepared by conventional treatment of the Formula I-IV compounds with suitable base, e.g. NaOH, KOH, CaO, etc. The quaternary salts can be prepared by conventional treatment of the Formula I-IV compound with an alkyl iodide such as methyl iodide, ethyl iodide and the like.

The acid addition salts can be prepared by conventional treatment of Formula I-IV compounds with a suitable inorganic or organic acid. Suitable inorganic acids are the hydrohalides, e.g. HCl, HI, HBr, sulfuric acid, phosphoric acid, and the like.

Suitable organic acids are exemplified by $C_2$-$C_{24}$ carboxylic acids such as acetic acid, tetracosanoic acid, oleic acid, 2-ethylhexoic acid, maleic acid, pamoic acid, lactic acid, citric acid, succinic acid, malic acid, trimethylacetic acid, oxalic acid, fumaric acid, cyclohexylcarboxylic acid, lauric acid and the like and non-carboxylic acids such as isenthionic acid.

The compounds of the present invention have antihypertensive activity and/or xanthine oxidase (X.O.) inhibiting activity. Some compounds have both activities.

The xanthine oxidase activity of representative compounds was determined using an in vitro test—the antihypertensive activity was determined by administration of said compounds to a spontaneously hypertensive (SH) or renal hypertensive (RH) rat. Results of such tests are tabulated below. The X.O. inhibition is expressed as % inhibition of the enzyme at a present compound concentration of $2 \times 10^{-5}$ M.

TABLE 1

| Antihypertensive (AH) and X.O. Inhibiting Activity | | |
|---|---|---|
| Compound | A.H. Activity | % X.O. Inhibition |
| ![structure] | yes[1] | 4 |

TABLE 1-continued
Antihypertensive (AH) and X.O. Inhibiting Activity

| Compound | A.H. Activity | % X.O. Inhibition |
|---|---|---|
| (6-methyl-2-(pyridyl)imidazole) | yes[1] | 0 |
| (5-chloro-benzimidazole with pyridyl) | yes[2] | 11 |
| (5,6-dichloro-benzimidazole with pyridyl) | no | 56 |
| (imidazo-pyridine with pyridyl) | yes[1] | 8 |
| (imidazo-pyridine with pyridyl) | yes[1] | 5 |
| (imidazo-pyridine with pyridyl) | yes[1] | 62 |
| (imidazo-pyridine with pyridyl) | no | 23 |

[1] = SH rat
[2] = RH rat

To demonstrate the unexpected improvement in antihypertensive activity conferred by the alkyl substituent on the pyridylimidazole moiety, comparative results were obtained for alkyl and non-alkyl pyridylimidazoles administered intraperitoneally to the spontaneously hypertensive rat. The comparative data is in the following table:

TABLE 2
COMPARATIVE ANTIHYPERTENSIVE DATA IN THE S H RAT

| Test | COMPOUND | DOSAGE (mg/kg) | Δ MAP[①] (mm/Hg) | Avg.Δ |
|---|---|---|---|---|
| A | (pyridyl-imidazole) | 20 | −1<br>−13 | −7 |
| B | (methyl-pyridyl-imidazole) | 20 | −31<br>−20 | −25 |

TABLE 2-continued
COMPARATIVE ANTIHYPERTENSIVE DATA IN THE S H RAT

| Test | COMPOUND | DOSAGE (mg/kg) | Δ MAP[①] (mm/Hg) | Avg.Δ |
|---|---|---|---|---|
| C | (methyl-pyridyl-imidazole) | 20 | −22<br>−10 | −16 |

[①]mean arterial pressure

The data in Table 2 clearly shows that the antihypertensive activity of an alkylsubstituted-2-pyridylimidazole is on average, 2–3½ times greater (Test C-Test B) than that of an unsubstituted-2-pyridylimidazole (Test A).

The xanthine oxidase inhibiting activity of the present compounds indicates that they will be useful for treating gout or hyperuricemia in human patients. Administration of the compounds for such treatment may be oral or parenteral, using appropriate dosage forms, e.g. tablets, capsules, sterile solutes, elixirs, etc. Daily dosage for this utility may be varied, ranging from about 30 mg. to about 1.5 gm., and preferably from about 100 to about 800 mg. The antihypertensive activity exhibited by the present compounds indicates that they will be useful for treating hypertension (lowering blood pressure) in human patients. Administration of the compounds may be oral or parenteral, e.g. intravenous, intraperitoneal, intramuscular, etc., using appropriate dosage forms, e.g. tablets, capsules, sterile solutions, emulsions, etc. Daily dosage for the utility may be varied ranging from about 10 mg. to about 1500 mg., preferably from about 100 mg. to about 1000 mg.

Compounds of Formula I are prepared by the reaction of an appropriate pyridinealdehyde with ammonia and $$R_1-\overset{O}{\underset{\|}{C}}-CH_2-O-\overset{O}{\underset{\|}{C}}-R_n$$

where $R_n$ is $C_1$–$C_5$ alkyl, in the presence of a suitable oxidizing agent such as a cupric salt e.g., the acetate. The following equation illustrates this reaction:

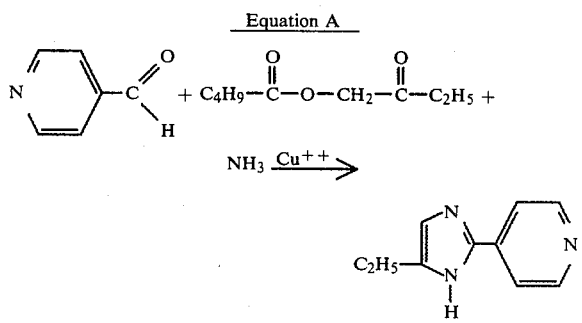

Equation A

Compounds of Formula II, III and IV are prepared by the reaction of an appropriate ortho diamine with nicotinic (pyridyl-3-carboxylic acid) or isonicotinic acid (pyridyl-4-carboxylic acid), either at elevated temperature, or at elevated temperature in the presence of an acid, e.g. polyphosphoric acid. The following equations illustrate the general reactions:

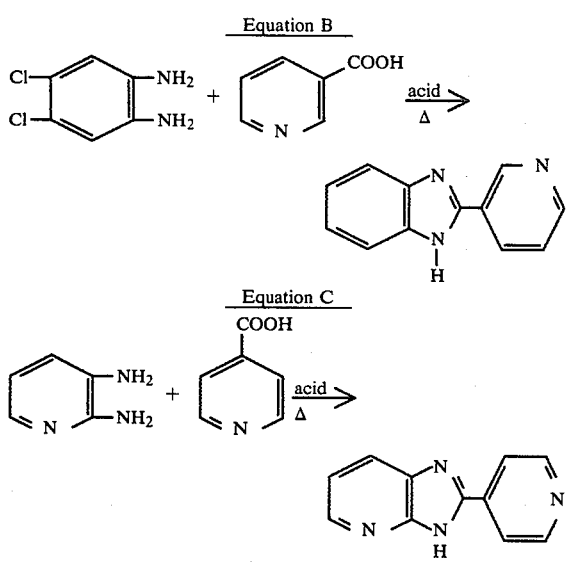

The following examples illustrate preparation of compounds of the present invention. All temperatures are in °C. unless otherwise specified.

EXAMPLE 1

Preparation of 4(5)-methyl-2-(4-pyridyl)imidazole

A solution of α-acetoxyacetone (3.5 g., 0.03 mol), $Cu(OAc)_2.H_2O$ (12 g., 0.06 mol) and pyridine-4-carboxaldehyde (3.2 g., 0.03 mol) in conc. $NH_4OH$ (75 ml) and MeOH (75 ml.) was heated 3 hr. at reflux. After cooling to room temperature, the precipitated solid was removed by filtration and resuspended in $H_2O$ at 80°. $H_2S$ was bubbled into the suspension for 1 hr. After filtration, the filtrate was saturated with $Na_2CO_3$ and extracted with $CHCl_3$. The $CHCl_3$ extract was dried over $Na_2SO_4$ and concentrated to dryness under reduced pressure. The resulting residue was chromatographed on alumina, activity grade II, and eluted with $CHCl_3$. After recrystallization from $H_3CCN$, 0.55 g. of 4(5)-methyl-2-(4-pyridyl)imidazole was obtained (12%); m.p. 154.5°–156°.

Using substantially the same procedure as Example 1 but substituting pyridine-3-carboxaldehyde for pyridine-4-carboxaldehyde, a 15% yield of 4(5)-methyl-2-(3-pyridyl)imidazole, melting at 166°–167° C., was obtained.

EXAMPLE 2

Preparation of 5-chloro-2-(4-pyridyl)benzimidazole

To a mixture of isonicotinic acid (4.9 g., 0.04 mol) and 4-chloro-o-phenylenediamine (5.8 g., 0.041 mol) was added polyphosphoric acid (20 ml.). The mixture was heated to 200° and maintained at this temperature for 45 min. After cooling, the reaction mixture was poured onto ice and the solution made basic with conc. $NH_4OH$. The resulting yellow solid was removed by filtration, dissolved in isopropanol, filtered and the filtrate concentrated to a solid. After recrystallization from EtOH-$H_2O$, 4.5 g. of 5-chloro-2-(4-pyridyl)benzimidazole (49.1%) was obtained; m.p. 306–307.

5,6-Dichloro-2-(4-pyridyl)benzimidazole melting at 297° C. was obtained (11.2% yield) using substantially the same procedure as Example 2, but substituting 4,5-dichloro-o-phenylene diamine for the 4-chloro-o-phenylene diamine.

5-Chloro-2-(3-pyridyl)benzimidazole melting at 244°–246° C. was obtained in 52.4% yield using substantially the same procedure as in Example 2, but substituting pyridine-3-carboxylic acid for the pyridine-4-carboxylic acid and recrystallizing from $H_3CCN$-EtOH instead of EtOH-$H_2O$.

EXAMPLE 3

Preparation of 2-(3-pyridyl)-1H-imidazo[4,5-b]pyridine

A mixture of 2,3-diaminopyridine (5.4 g., 0.05 mol) and nicotinic acid (6.1 g., 0.05 mol) was heated at 240° for 30 min. The resulting dark melt was allowed to cool and then recrystallized four times from MeOH-$H_2O$ to yield 1.5 g. of 2-(3-pyridyl)-1H-imidazo[4,5-b]pyridine (15.3%); m.p. 284°.

Using substantially the same procedure as in Example 3, the following reactants produced the imidazopyridines as indicated. All the products were recrystallized from $H_3CCN$-$H_2O$.

| Reactants | Product | M.P. | Yield |
|---|---|---|---|
| 3,4-diamino-pyridine and pyridine-3-carboxylic acid | 2-(3-pyridyl)-1H-imidazo[4,5-c]-pyridine | 247°–249° C. | 20.4% |
| 2,3-diamino-pyridine and pyridine-4-carboxylic acid | 2-(4-pyridyl)-1H-imidazo-[4,5-c]pyridine | 297° C. | 11.2% |
| 3,4-diamino-pyridine and pyridine-4-carboxylic acid. | 2-(4-pyridyl)-1H-imidazo-[4,5-c]pyridine | 285°–286° C. | 15.3% |

Claims to the invention follow.
What is claimed is:
1. A compound having the formula

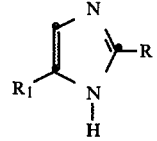

wherein R is 4-pyridyl and $R_1$ is $C_1$-$C_5$ alkyl or pharmaceutically acceptable salt thereof.

2. Compound of claim 1 wherein said salt is an acid addition salt.

3. Compound of claim 1 having the formula

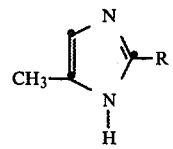

4. A pharmaceutical composition for treating hypertension containng an effective amount of a compound selected from the group consisting of
2-(4-pyridyl)-5-methylimidazole, and
pharmaceutically acceptable salt thereof.

5. Method of treating hypertension in humans which comprises administering an effective amount of compound of claim 1.

6. The method of claim 5 wherein said amount is about 10 mg. to about 1500 mg. per day.

* * * * *